US012569433B2

(12) United States Patent
Shade et al.

(10) Patent No.: US 12,569,433 B2
(45) Date of Patent: Mar. 10, 2026

(54) MICROEMULSION DELIVERY SYSTEMS FOR WATER-BASED BEVERAGES

(71) Applicant: Quicksilver Scientific, Inc., Louisville, CO (US)

(72) Inventors: Christopher W. Shade, Louisville, CO (US); Steven Tieu, Louisville, CO (US)

(73) Assignee: Quicksilver Scientific, Inc., Louisville, CO (US)

( * ) Notice: Subject to any disclaimer, the term of this patent is extended or adjusted under 35 U.S.C. 154(b) by 889 days.

(21) Appl. No.: 17/673,086

(22) Filed: Feb. 16, 2022

(65) Prior Publication Data

US 2022/0241192 A1 Aug. 4, 2022

Related U.S. Application Data

(63) Continuation of application No. PCT/US2020/049155, filed on Sep. 3, 2020.
(Continued)

(51) Int. Cl.
*A61K 9/00* (2006.01)
*A61K 9/107* (2006.01)
(Continued)

(52) U.S. Cl.
CPC .......... *A61K 9/0095* (2013.01); *A61K 9/1075* (2013.01); *A61K 31/01* (2013.01);
(Continued)

(58) Field of Classification Search
CPC .... A61K 9/0095; A61K 9/1075; A61K 31/01; A61K 31/015; A61K 31/045;
(Continued)

(56) References Cited

U.S. PATENT DOCUMENTS 6,267,985 B1 7/2001 Chen et al.
8,628,796 B2 1/2014 Kottayil et al.
(Continued)

FOREIGN PATENT DOCUMENTS

CA 2982250 A1 9/2016
CA 3038473 A1 4/2018
(Continued)

OTHER PUBLICATIONS

European Patent Office , "Supplementary European Search Report", Application No. 20861694.6, Aug. 17, 2023, 11 pages.
(Continued)

*Primary Examiner* — Deborah D Carr
(74) *Attorney, Agent, or Firm* — Blanchard Horton PLLC

(57) ABSTRACT

Microemulsion beverages are described where hydrophobic liquid droplets are distributed in a continuous hydrophilic liquid phase. The described microemulsion beverages may be thought of as modified oil-in-water (MOIHW) microemulsions, where both the "oil" and "water" phases of the microemulsion are modified. The oil phase droplets of the MOIHW microemulsion are modified with alcohol and can solubilize oil-soluble species, including cannabis extracts. The polar continuous "water" phase of the MOIHW microemulsion is modified with a sugar or sugar alcohol.

61 Claims, 4 Drawing Sheets

Nanoemulsion Droplet

Related U.S. Application Data

(60) Provisional application No. 62/896,861, filed on Sep. 6, 2019.

(51) Int. Cl.

| | |
|---|---|
| *A61K 31/00* | (2006.01) |
| *A61K 31/01* | (2006.01) |
| *A61K 31/015* | (2006.01) |
| *A61K 31/045* | (2006.01) |
| *A61K 31/07* | (2006.01) |
| *A61K 36/185* | (2006.01) |
| *A61K 47/10* | (2017.01) |
| *A61K 47/14* | (2017.01) |
| *A61K 47/24* | (2006.01) |
| *A61K 47/26* | (2006.01) |
| *A61K 47/44* | (2017.01) |

(52) U.S. Cl.

CPC .......... *A61K 31/015* (2013.01); *A61K 31/045* (2013.01); *A61K 31/07* (2013.01); *A61K 31/658* (2023.05); *A61K 36/3482* (2024.05); *A61K 47/10* (2013.01); *A61K 47/14* (2013.01); *A61K 47/24* (2013.01); *A61K 47/26* (2013.01); *A61K 47/44* (2013.01)

(58) Field of Classification Search

CPC ...... A61K 31/05; A61K 31/07; A61K 31/352; A61K 47/10; A61K 47/14; A61K 47/24; A61K 47/26; A61K 47/44; A61K 31/658; A61K 36/185; A23L 2/52; A23L 2/62; A23L 2/68; A23L 2/56

See application file for complete search history.

(56) References Cited

U.S. PATENT DOCUMENTS

| | | | |
|---|---|---|---|
| 9,629,886 B2 | 4/2017 | Franklin et al. | |
| 2014/0348926 A1 | 11/2014 | Hoffman et al. | |
| 2016/0058866 A1 * | 3/2016 | Sekura | A61K 9/006 |
| | | | 514/454 |
| 2016/0081976 A1 | 3/2016 | Bromley | |
| 2018/0042845 A1 | 2/2018 | Sinai et al. | |

FOREIGN PATENT DOCUMENTS

| | | | | |
|---|---|---|---|---|
| CA | 2937471 | A1 | 2/2019 | |
| CA | 3151663 | | 8/2025 | |
| CN | 102309445 | A | 3/2013 | |
| EP | 1437136 | A1 | 7/2004 | |
| EP | 2314284 | A2 | 4/2011 | |
| EP | 2596705 | A1 | 5/2013 | |
| WO | 0133573 | A1 | 5/2001 | |
| WO | 2008039564 | A1 | 4/2008 | |
| WO | 2011128630 | A2 | 10/2011 | |
| WO | 2016086735 | A1 | 11/2016 | |
| WO | 2017182950 | A1 | 10/2017 | |
| WO | WO-2018061007 | A1 * | 4/2018 | .......... A61K 31/015 |
| WO | 2018152334 | A1 | 8/2018 | |
| WO | 2021046189 | A1 | 3/2021 | |

OTHER PUBLICATIONS

Innovation Science & Econ Dev CA , "Examination Report under Subsection 86(2)", App. No. 3,151,663, Sep. 28, 2023, 3 pages.

Cunningham, Courtney A., et al., "Propylene Glycol Poisoning From Excess Whiskey Ingestion: A Case of High Osmolal Gap Metabolic Acidosis", Journal of Investigative Medicine High Impact Case Reports; Jul.-Sep. 2015: 1-2 © 2015 American Federation for Medical Research; DOI: 10.1177/2324709615603722; hic.sagepub. com, Jul. 2015, 2 Pages.

Mitchell, M C, et al., "Absorption and peak blood alcohol concentration after drinking beer, wine, or spirits.", Mitchell et al., Absorption and Peak Blood Alcohol Concentration After Drinking Beer, Wine, or Spirits, Alcohol Clin Exp Res, vol. 38, No. 5 (2014); pp. 1200-1204, May 2014, 1200-1204.

Vandrey, Ryan , et al., "Pharmacokinetic Profile of Oral Cannabis in Humans: Blood and Oral Fluid Disposition and Relation to Pharmacodynamic Outcomes", THC blood concentrations and time after consumption of an oil-based delivery system (brownie) taken from Vandrey et al., Pharmacokinetic Profile of Oral Cannabis in Humans: . . . , Journal of Analytical Toxicology, vol. 41 (2017); pp. 83-99, Feb. 3, 2017, 83-99.

* cited by examiner

Microemulsion
Droplet

Nanoemulsion
Droplet

300

310 — Combine Oil-Soluble Species 311 into an Alcohol Lipid Mixture 312

320 — Combine the Alcohol Lipid Mixture 312 Including the Oil-Soluble Species 311 with a Modified Polar Continuous Phase 322

330 — Form a Microemulsion 336 at Atmospheric Pressure

340 — Combine the Microemulsion 336 with Sufficient Water to Form a High-Water Content Beverage 342 Including at Least 95% Water by Weight

MICROEMULSION DELIVERY SYSTEMS FOR WATER-BASED BEVERAGES

REFERENCE TO RELATED APPLICATIONS

This application is a continuation of International Application No. PCT/US20/49155, entitled "Microemulsion Delivery Systems for Water-Based Beverages", filed Sep. 3, 2020, which claims the benefit of U.S. Provisional Application No. 62/896,861 entitled "Microemulsion Delivery Systems for Water-Based Beverages" filed Sep. 6, 2019, both of which are incorporated by reference in the entirety.

BACKGROUND

Cannabinoids are compounds that act on the cannabinoid receptors in cells that alter neurotransmitter release. Cannabinoids include the endocannabinoids, which are produced naturally in the bodies of animals, phytocannabinoids, which are found in plants of the *Cannabis* genus and in some other plants, and synthetic cannabinoids that are synthesized. Type 1 cannabinoid receptors are found primarily in the brain and are absent from the part of the brain stem responsible for respiratory and cardiovascular function. Type 2 cannabinoid receptors are predominantly found in the immune system and appear to be responsible for the anti-inflammatory and possibly other therapeutic effects.

Phytocannabinoids are isolated from plants of the *Cannabis* genus, which is believed to include three species, *Cannabis sativa, Cannabis indica*, and *Cannabis ruderalis*. *Cannabis* plants including less than 0.3% tetrahydrocannabinol (THC) by weight are commonly referred to as "hemp", while plants including 0.3% or greater by weight THC are commonly referred to as "marijuana". At least 113 different phytocannabinoids may be isolated from plants of the *Cannabis* genus. The phytocannabinoids are isolated in their "A" or acidic form and are then decarboxylated, often by heat, to their more biologically active, decarboxylated forms.

Cannabidiol (CBD) is becoming a more commonly known non-psychoactive cannabinoid as it acts on the Type 1 and Type 2 receptors and is known to reduce pain and inflammation and calm some nerve responses, such as those associated with Dravet syndrome in children. Additionally, CBD may counteract cognitive impairment associated with THC use, including short term memory loss and may have additional anti-psychotic effects in addition to serving as an antioxidant.

THC is the most famous cannabinoid as it binds to the Type 1 receptors and is considered psychoactive. THC has the ability to provide a happy or relaxed feeling, to alter time and sensory perception, and to increase appetite. However, without controlled dosing, negative effects including anxiety, confusion, and paranoia can result. As different individuals experience the transition from "good" to "not-so-good" at different dosing levels, a key goal of a THC delivery system should be to provide the ability to consistently control dosing. Thus, if a THC delivery system can reproducibly provide a known bloodstream concentration in a known timeframe, the consumer can knowingly control their intake over time.

The ability of a consumer to reproducibly control dosing has been a key difference between the consumption of marijuana versus alcohol-based beverages. When people consume alcohol-based beverages they understand that a shot of liquor has about the same alcohol content as a glass of wine or a beer. The body transfers alcohol from the stomach to the bloodstream relatively rapidly and at similar rates whether the alcohol is in liquor, wine, or beer form. For example, liquor consumed on an empty stomach provides a peak blood alcohol concentration (BAC) after 30 minutes, while the peak BAC for wine and beer occurs after approximately an hour. While different individuals may have different effects from a given volume of alcohol, whatever effect that individual experiences from a given volume of alcohol-based beverage is relatively reproducible across the spectrum of available alcohol-based beverages.

This consumption/effect relationship that all alcohol-based beverage consumers have or soon develop with repeat consumption is absent from the conventional THC delivery systems. At the outset, there is the question of how much THC is present in any given portion of a marijuana plant or extract. Secondly, unlike alcohol, cannabinoids, including CBD and THC, are not water soluble, instead being oil soluble. Thus, directly adding oil soluble cannabinoids to water-based liquids results in the oil soluble dissociating from the water and adhering to the sides of the container or if the oil soluble reaches the stomach, being processed along with other oils.

In direct contrast to water soluble alcohol, THC's oil solubility means that an extremely variable uptake rate after consumption may be experienced depending on the delivery system, and for that matter, on whether the individual's digestive tract is empty or full of oil containing food. While food can somewhat alter the rate of alcohol uptake, the alteration that occurs with oil soluble THC is substantially greater. Thus, while the primary controller of bloodstream THC concentrations at a post-consumption time is the THC concentration of the plant or extract for inhaled THC delivery systems, the THC concentration of the plant or extract is only one factor for orally consumed THC delivery systems.

Food-based THC delivery systems, including brownies, gummies, desserts, and other edibles, generally rely on one or more oils in the food to solubilize the THC and to deliver the THC with the other oily constituents of the food to the digestive tract. While the THC concentration in the delivery oil can be controlled during manufacturing, an issue with these oil-based delivery systems is that they do not produce sufficient bloodstream concentrations of the THC rapidly enough for the individual to feel the effect of the THC until substantial time has lapsed after consumption. Furthermore, due the previously described wide variance in bloodstream delivery rates of oil-based delivery systems, such oil-based systems provide poor dosing reproducibility. So, both the time to effect and the level of effect experienced in relation to the amount of THC consumed lack reproducibility for orally consumed THC delivery systems.

Thus, a consumer of THC attempting to control their individual consumption/effect relationship with orally consumed THC delivery systems has two significant impediments. First, unlike with the consumption of alcohol, which has a rapid onset of approximately 15 to 30 minutes with a peak bloodstream delivery time of approximately 30 to 45 minutes, for oil-based THC delivery systems the initial onset of feeling the effect of the THC is delayed until approximately 30 to 60 minutes with a peak bloodstream delivery time of approximately 1.5 to 3 hours. Thus, the consumer has little ability to initially or during continued THC consumption control the effect because it is extremely difficult to manage the "consume X amount now to have Y effect later—and exactly when will later be" relationship. For example, a consumer may feel no effect from consumed THC until after an hour, and may not feel the maximum effect from the initial consumption for 3 hours.

Second, unlike with the consumption of alcohol where nearly all alcohol consumed reaches the bloodstream, and is thus experienced, the wide variability in what percent of the orally consumed THC is delivered to the bloodstream by the oil-based delivery system prevents the consumer from repro- ducibly predicting what the latter maximum effect will be, whenever it does occur, which can lead to undesirable overdosing. Thus, with conventional oil-based THC delivery systems, it is nearly impossible for a consumer to reproduc- ibly manage the consumption/effect relationship for THC consumption across different consumables as is readily done with alcohol consumption.

Conventional cannabinoid tinctures are available on the market that include some combination of cannabinoid, oil, and alcohol. Such tinctures can be consumed intra-orally or may be added to beverages or food prior to consumption. However, these systems are fundamentally lowered viscos- ity oil-based delivery systems having the associated slow and unpredictable uptake of oil-based delivery systems.

Recently, high-water content beverages have entered the market that include cannabinoids including THC. These beverages may be made by forming a nanoemulsion using high-pressure shear forces to disperse an oil containing THC mixture into water. However, such products are not-shelf stable and if initially visually clear, will lose such clarity with time as the high-pressure sheared oil droplets dissociate from the water by increasing in size and/or eventually precipitating to form solids. Neither are these beverages optimized for intra-oral delivery. Thus, while these bever- ages may be attempting to address the issue of a THC consumer's inability to effectively manage their individual consumption/effect relationship or at least provide cannabi- noids in beverage form, significant disadvantages remain.

Emulsions are mixtures of two or more liquids that do not solubilize. Thus, the two or more liquids do not form a solution and an identifiable interface exists between the combined liquids. Emulsions may be macroemulsions, pseudo-emulsions, nanoemulsions or microemulsions. Emulsions may be used for parenteral delivery, ocular delivery, transdermal delivery, oral delivery, and the like.

FIG. 1A represents an example nanoemulsion droplet 100 having a single wall of phospholipids (monolayer) forming a hydrophilic exterior 120 and a hydrophobic interior 110. The monolayer wall of the nanoemulsion droplet 100 is formed from a single layer of phospholipids. The outer wall 120 is water soluble due to the phosphate functionality while the interior 110 is fat-soluble due to the alkyl functionality. FIG. 1B represents multiple of the nanoemulsion droplets 100 in a continuous phase 150.

FIG. 2A represents a microemulsion droplet 200 having a single wall of phospholipids (monolayer) forming a hydro- philic exterior 220 and a hydrophobic interior 210. As with the nanoemulsion droplets 100, the monolayer wall of the microemulsion droplet 200 is formed from a single layer of phospholipids. In relation to the represented nanoemulsion droplets 100, the microemulsion droplets 200 are substan- tially smaller in diameter—which is often the case for microemulsions. In fact, the diameter of the microemulsion droplets 200 are reduced to where non-polar tails 230 of the monolayer phospholipids are "crushed" into each other, thus forming a more "solid" interior hydrophobic barrier than in the case of the nanoemulsion droplets 100 as represented in FIG. 1. FIG. 2B represents multiple microemulsion droplets 200 in a continuous phase 250. Also represented in the continuous phase 250 are a few individual phospholipid molecules 260 not incorporated into the microemulsion droplets 200.

While the high-energy mixing, in the form of pressure (including shear forces), temperature, and combinations thereof, used to form nanoemulsions can provide the smaller droplets of a microemulsion, such nanoemulsions are not thermally stable, thus are not shelf-stable microemulsions, and are like a macroemulsion in that the components of the nanoemulsion eventually separate into immiscible polar and non-polar liquids. Thus, as represented in FIG. 1 and FIG. 2, nanoemulsion droplets tend to be larger than microemulsion droplets as the nanoemulsion droplets continually expand in diameter after formation until the agglomerating droplets separate from the continuous phase.

Conventionally, macroemulsions, nanoemulsions, and microemulsions have been used for either oil-soluble or water-soluble deliverables. *Cannabis* extracts are oil- soluble, but are absorbed relatively slowly and inconsis- tently through the gut when solubilized in oil. Furthermore, the concentrations of cannabis extracts that may be success- fully solubilized in oil alone is often low, requiring a relatively large volume of carrier oil to solubilize the can- nabis extract. This problem is exasperated in the instance of high-water content beverages, where the higher oil concen- trations required to carry sufficient cannabis extract in the shear-formed nanoemulsion beverage result in undesirable taste and visual clarity in addition to speeding the dissocia- tion of the oil from the water of the unlikely to be shelf- stable nanoemulsion.

Conventional oil-in-water (OIW) emulsions also tend to suffer from similar disadvantages to oil only delivery for- mulations regarding delayed bloodstream uptake. This is believed attributable to conventional oil-in-water emulsions including cannabis extracts forming oil droplets that readily dissociate from the water phase of the emulsion at higher concentrations of cannabis extracts in the oil droplets. Such dissociation of the oil droplets from the water phase results in a delivery profile for the oil dissociated emulsion approxi- mating the oil only formulation, which is slow and incon- sistent, as the primary delivery component of the oil disso- ciated emulsion is the oil alone. Thus, the cannabinoids may lose significant blood uptake rate and total blood delivery when delivered in oils and in conventional OIW emulsions as the oil phase has may significantly dissociate from the water phase by the time the conventional OIW nanoemul- sion is consumed.

As can be seen from the above description, there is an ongoing need for simple and efficient materials and methods for oral delivery systems for delivering cannabinoids quickly and in higher, reproducible concentrations per con- sumed amount to the bloodstream. Conventional oil mix- tures have traditionally been plagued with exceedingly slow, low, and inconsistent uptake attributed to the GI adsorption pathway. Conventional oil-in-water emulsion systems have traditionally had disadvantages including poor stability to cold and heat, particularly regarding maintaining the desired average droplet diameter in the emulsion, which is important for effective intra-oral delivery to the bloodstream, prevent- ing phase separation of the oil and water components, and preventing dissociation of the deliverable and/or the oil from the emulsion. In addition to these disadvantages resulting in slow, poor, and inconsistent blood uptake of the deliverable, conventional emulsion systems also have the disadvantage of requiring too great a volume of the oil portion in relation to the water portion of the emulsion.

The microemulsions and methods of the present invention overcome at least one of the disadvantages associated with conventional OIW beverage systems by allowing the convenient, rapid, efficient, and reproducible oral delivery of cannabinoids to the bloodstream via a high-water content beverage.

SUMMARY

In one aspect, the invention provides a composition including an oil-soluble species; and a modified oil-in-water microemulsion including a modified oil phase and a modified polar continuous phase, where the oil-soluble species is solubilized in the modified oil phase, the modified oil phase comprising a phospholipid, a polyethylene glycol derivative, an oil, and an alcohol, where the modified polar continuous phase includes a sugar or sugar alcohol and water, and where the high-water content beverage comprises at least 95% water by weight.

In another aspect of the invention, there is a method of forming a high-water content beverage, the method including combining a phospholipid, a polyethylene glycol derivative, an oil, and an alcohol to form an alcohol-lipid mixture; combining a sugar or sugar alcohol and a first aliquot of water to form a modified polar continuous phase; combining an oil-soluble species with the alcohol-lipid mixture and the modified polar continuous phase at atmospheric pressure to form an intermediate low-water content modified oil-in-water microemulsion; combining the intermediate low-water content modified oil-in-water microemulsion with a second aliquot of water to provide a high-water content beverage.

In another aspect of the invention, there is a method of delivering an oil-soluble species to the bloodstream of a human subject, the method including introducing a high-water content beverage composition orally to a human subject; and delivering the oil-soluble species to the bloodstream of the human subject, where within 40-minutes of the introducing the composition, the human subject has an oil-soluble species blood concentration in excess of one ppb when the high-water content beverage composition includes 3 mg of the oil-soluble species.

In another aspect of the invention, there is a high-water content, visually clear, and shelf-stable beverage composition, the composition including a cannabinoid extract; a phospholipid; a polyethylene glycol derivative; an oil; an alcohol; a sugar or sugar alcohol; and at least 95% water by weight.

Other systems, methods, features, and advantages of the invention will be, or will become, apparent to one with skill in the art upon examination of the following figures and detailed description.

BRIEF DESCRIPTION OF THE DRAWINGS

The invention can be better understood with reference to the following drawings and description. The components in the figures are not necessarily to scale and are not intended to accurately represent molecules or their interactions, emphasis instead being placed upon illustrating the principles of the invention.

DETAILED DESCRIPTION

Figures 1A, 1B, 2A, 2B:
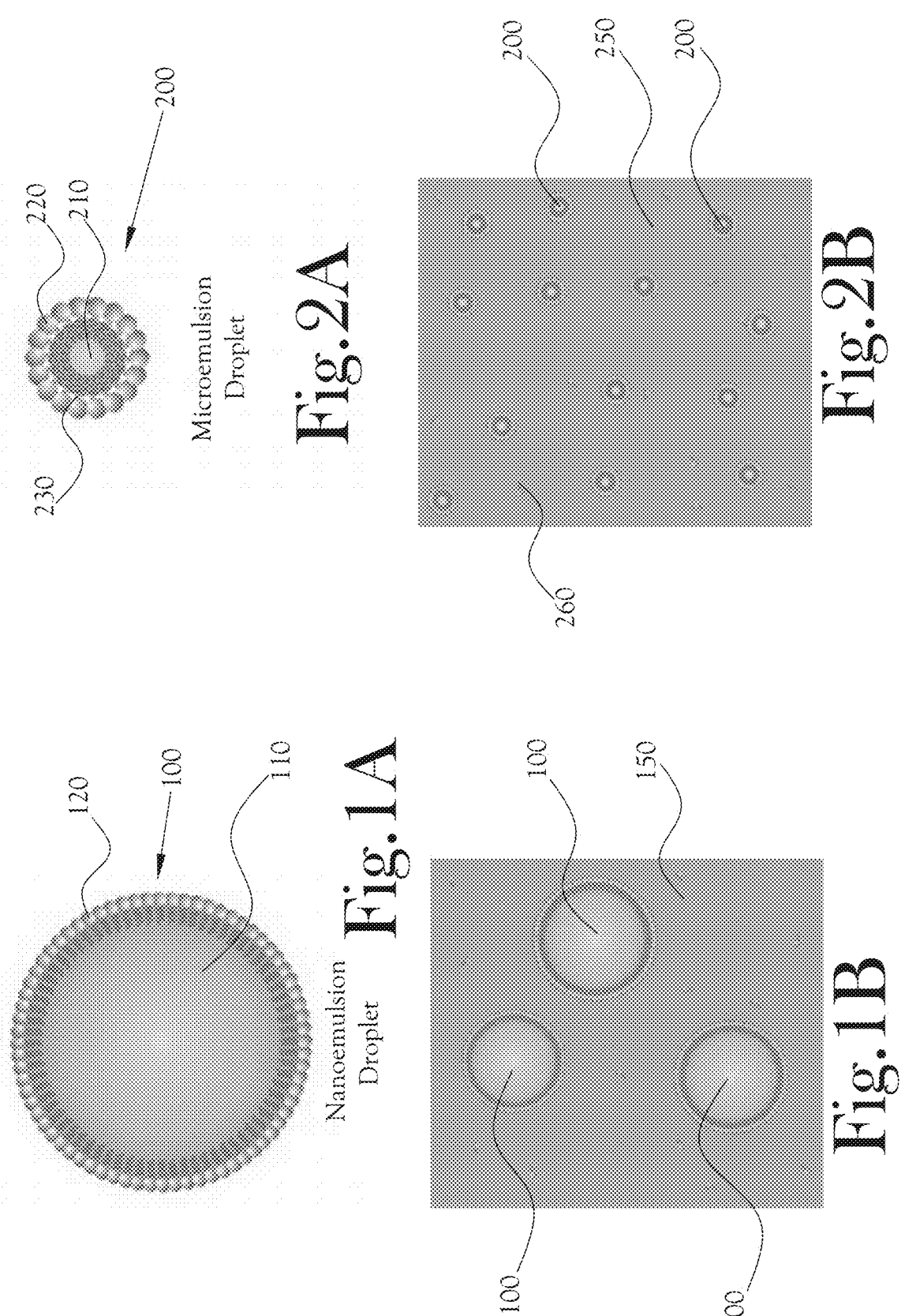
FIG. 1A represents a nanoemulsion droplet having a single wall of phospholipids (monolayer) forming a hydrophilic exterior and a hydrophobic interior.
FIG. 1B represents multiple of the nanoemulsion droplets in a continuous phase.
FIG. 2A represents a microemulsion droplet having a single wall of phospholipids (monolayer) forming a hydrophilic exterior and a hydrophobic interior.
FIG. 2B represents multiple microemulsion droplets represented in a continuous phase.

Microemulsions are described where hydrophobic liquid droplets are distributed in a continuous hydrophilic liquid phase. In relation to conventional oil-in-water (OIW) microemulsions, the described microemulsions may be thought of as modified oil-in-high-water content (MOIHW) microemulsions, where both the "oil" and "water" phases of the microemulsion are modified and the water phase constitutes at least 95% of the microemulsion by weight. Due to the high-water content of the MOIHW microemulsion, the microemulsion is suitable for consumption as a beverage. The beverage may be carbonated or non-carbonated and include taste and color modifiers that are compatible with the MOIHW microemulsion forming the beverage.

The oil phase droplets of the MOIHW microemulsion are modified with alcohol and can better deliver oil-soluble species to the bloodstream than can oil blends and can form shelf-stable and visually clear high-water content beverages that carry higher concentrations of cannabis extract per beverage volume than conventional oil-in-water (OIW) emulsions. The polar, continuous high-water content "water" phase of the MOIHW microemulsion is modified with a sugar or sugar alcohol, thus providing a modified polar continuous phase. The modified oil phase droplets disperse into the modified polar continuous phase of the MOIW microemulsion.

Furthermore, the oil to phospholipid/polyethylene glycol derivative ratio of the MOIHW microemulsion can be "tuned" to provide a bloodstream uptake rate of the oil-soluble species to be rapid, thus approximating the alcohol uptake rate, delayed, thus approximating the oil-based delivery system uptake rate, or a combination of both. In this way, the MOIHW microemulsion can provide a beverage resulting in relatively rapid effect onset and decay, similar to alcohol, or resulting in an effect combining the relatively rapid effect onset of alcohol coupled with the extended effect of an oil-based delivery system. Such a dual-delivery profile or an oil-based delivery profile may be preferred for the medicinal as opposed to recreational use of a beverage. In this way, a dual-delivery mode beverage could provide the medicinal effects of THC regarding anti-nausea and/or pain relief, for example, with a delivery profile similar to a tablet delivery form—potentially with a slightly more rapid effect onset.

The MOIHW microemulsions can provide the uptake of the oil-soluble species to the bloodstream of a human primarily trans-mucosally through the oral and gastric mucosa and/or through the stomach and intestines. The MOIHW microemulsion including the oil-soluble species is ingestible and edible.

The MOIHW microemulsion can orally deliver effective concentrations of the oil-soluble species to the bloodstream of a consumer faster, such as within 20-minutes of introduction, than the oil phases of conventional OIW emulsions, and can be tuned to also provide extended or primarily extended uptake. Also, of the oil-soluble species introduced, the MOIHW microemulsion can deliver a significantly higher percentage of the oil-soluble species introduced orally to the bloodstream of the individual than the oil phases of conventional OIW emulsions, including conventional OIW nanoemulsions that have dissociated to form relatively large average droplet diameter oil droplets in relation to the average droplet diameter of the MOIHW microemulsion.

The hydrophobic portion of the monolayer wall formed from the tails of the phospholipid and in combination with the polyethylene glycol derivative during initial formation, thus before dilution with water to form the high-water content beverage are believed to reduce alcohol loss from the oil droplets in relation to conventional OIW emulsions.

The retained high alcohol content of the modified oil phase droplets provided by the initially formed hydrophobic monolayer is believed to increase the solubility of the oil-soluble species in the modified oil droplets of the MOIW microemulsion in relation to conventional OIW emulsions. This enhanced solubility of the oil-soluble species in the modified oil droplets of the MOIHW is believed to reduce dissociation (e.g. recrystallization, precipitation, and like— thus separation) of the oil-soluble species from the oil droplets of the MOIHW microemulsion during storage, thus making the MOIHW microemulsion a shelf-stable microemulsion that is preferably visually clear. Additionally, the enhanced solubility of the oil-soluble species in the modified oil droplets of the MOIW is believed to deliver a greater amount of the oil-soluble species to the bloodstream per unit volume of the MOIHW microemulsion in relation to conventional OIW emulsions.

The MOIHW microemulsion includes modified oil phase droplets including the oil-soluble species having an average droplet diameter of 1 to 80 nanometers. The MOIHW microemulsion also may include modified oil phase droplets including the oil-soluble species having an average droplet diameter of 90 to 300 nanometers in the instance of a dual-delivery mode MOIHW microemulsion. Thus, due to the tunability of the delivery profile of the MOIHW microemulsion, the average droplet diameter of the MOIHW microemulsion may arise from an approximate bimodal distribution of average droplet diameters. Preferably, the MOIHW microemulsion includes at least one significant average droplet diameter population of 5 to 75 nanometers. More preferably, the MOIHW microemulsion includes at least one significant average droplet diameter population of 10 to 40 nanometers.

The MOIHW microemulsion preferably includes a ratio of phospholipid, to oil, to polyethylene glycol derivative, to alcohol, to sugar or sugar alcohol, and to water of 0.001-0.3:0.001-0.6:0.001-0.6:0.002-1.2:0.003-2.4:≥95 by weight, with deviations up to 10% by weight being included, and with deviations up to 5% by weight being more preferred, thus 0.001-0.3:0.001-0.6:0.001-0.6:0.002-1.2:0.003-2.4:≥95±10% by weight or 0.001-0.3:0.001-0.6:0.001-0.6:0.002-1.2:0.003-2.4:≥95±5% preferred by weight, when the MOIHW microemulsion includes at least 95% water.

The MOIHW microemulsion preferably includes a ratio of phospholipid, to oil, to polyethylene glycol derivative, to alcohol, to sugar or sugar alcohol, and to water of 0.002-0.04:0.001-0.4:0.001-0.4:0.002-0.8:0.003-1.6:≥97 by weight, with deviations up to 10% by weight being included, and with deviations up to 5% by weight being more preferred, thus 0.002-0.2:0.001-0.4:0.001-0.4:0.002-0.8:0.003-1.6:≥97±10% by weight or 0.002-0.2:0.001-0.4:0.001-0.4:0.002-0.8:0.003-1.6:≥97±5% preferred by weight, when the MOIHW microemulsion includes at least 97% water.

The MOIHW microemulsion preferably includes a ratio of phospholipid, to oil, to polyethylene glycol derivative, to alcohol, to sugar or sugar alcohol, and to water of 0.003-0.05:0.001-0.1:0.001-0.1:0.002-0.2:0.003-0.4:≥99 by weight, with deviations up to 10% by weight being included, and with deviations up to 5% by weight being more preferred, thus 0.003-0.05:0.001-0.1:0.001-0.1:0.002-0.2:0.003-0.4:≥99±10% by weight or 0.003-0.05:0.001-0.1:0.001-0.1:0.002-0.2:0.003-0.4:≥99±5% preferred by weight, when the MOIHW microemulsion includes at least 99% water.

The oil-soluble species is preferably included in the MOIHW microemulsion at a ratio of oil to oil-soluble species of 1:0.05 to 0.5 by weight, with a ratio of oil to oil-soluble species of 1:0.1 to 0.4 by weight being preferred with deviations up to 5% by weight being included, and with deviations up to 3% by weight being more preferred, thus 1:0.2 to 0.4±5% by weight or 1:0.2 to 0.4±3% preferred by weight.

Figure 3:
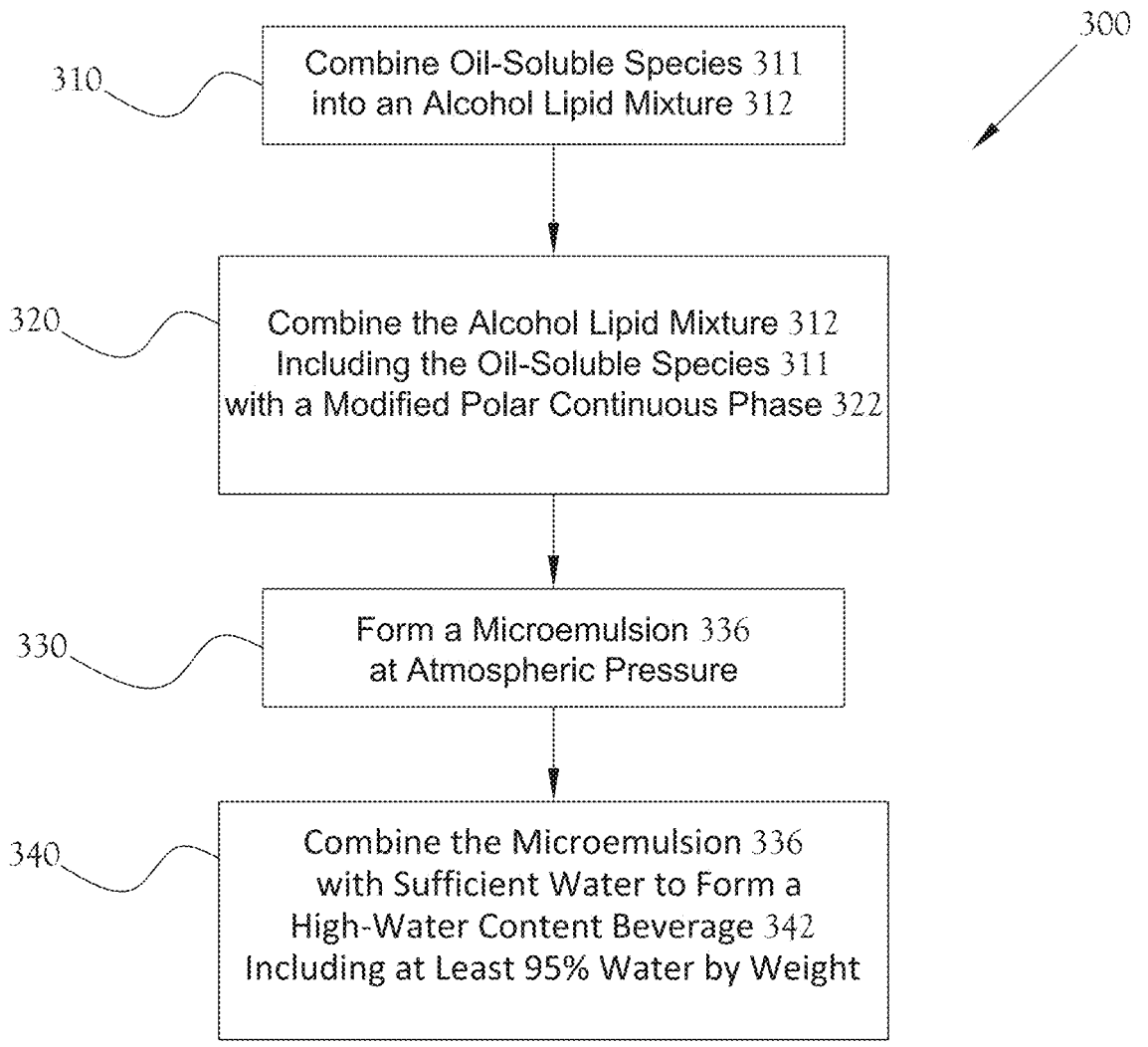
FIG. 3 represents a method of making a high-water content beverage in the form of a MOIHW microemulsion including an oil-soluble species.

FIG. 3 represents a method 300 of making a high-water content beverage 342 in the form of a MOIHW microemulsion including an oil-soluble species 311. In addition to the oil-soluble species 311, the beverage 342 may include additional ingredients that are soluble in water or oil.

In 310, the oil-soluble species 311 is combined into an alcohol-lipid mixture 312 including a polyethylene glycol derivative, a phospholipid, an oil, and an alcohol. In 320, the alcohol-lipid mixture 312 including the oil-soluble species 311 is combined with a modified polar continuous phase 322 including the sugar or sugar alcohol and water. The alcohol-lipid mixture 312 including the oil-soluble species 311 may be considered a modified oil phase dispersed in the modified polar continuous phase 322, which may be thought of as a modified water phase.

In 330, an intermediate low-water content microemulsion 336 including the oil-soluble species 311 is formed by mixing at atmospheric pressure. Unlike in nanoemulsions, the microemulsion 336 may be formed at atmospheric pressure without needing the energy of elevated pressures and/or shear forces to form. Although the microemulsion 336 could be formed using elevated pressure and/or shear forces as used in forming nanoemulsions, the result eventually will be the microemulsion 336, as unlike in a nanoemulsion that begins the dissociation process after formation—even if dissociation is very slow, the microemulsion 336 is thermally stable at room temperature and pressure after formation. Thus, formation of the microemulsion 336 dispenses with the undesirable use of elevated pressures and/or shear forces during formation, and is shelf-stable after formation.

In 340, the microemulsion 336 is combined with sufficient water to form the high-water content beverage 342 in the form of a MOIHW microemulsion including at least 95% water by weight.

While the method 300 represents the oil-soluble species 311 first being combined with the alcohol-lipid mixture 312, the alcohol-lipid mixture 312 and the polar continuous phase

322 may first be combined and the oil-soluble species 311 then added to form the microemulsion 336 (not shown). This step rearrangement is possible as the modified oil and modified polar continuous phases will "self-assemble" droplets including the oil-soluble species to form the microemulsion 336 at atmospheric pressure.

The oil-soluble species 311 is a liquid at room temperature and pressure, however at high purities, such as above 55% purity by weight, the oil-soluble species 311 may be or may include a crystalline solid. Once solubilized in oil, the oil-soluble species 311 will remain solubilized in the oil at room temperature and pressure. The oil-soluble species 311 preferably includes cannabis extracts, terpenes, and/or oil-soluble vitamins.

The oil-soluble species 311 is initially solubilized in the droplets of the microemulsion 336, thus in the alcohol-lipid mixture 312. The alcohol-lipid mixture 312 is preferably configured so that the oil-soluble species 311 is more soluble in the alcohol-lipid mixture 312 than in the oil alone of the microemulsion 336.

Preferably, the oil-soluble species 311 constitutes from 0.0001% to 0.24% of the high-water content beverage 342 by weight. However, to provide a visually clear beverage emulsion with the widest range of oil-soluble species, weight percentages of the oil-soluble species 311 from 0.0001% to 0.16% are preferred, with weight percentages from 0.0001% to 0.04% being more preferred. These stated weight percentages for the oil-soluble species 311 are in the context of the oil-soluble species 311 solubilized in the droplets of the high-water content beverage 342, not suspended in the continuous phase or otherwise dissociated from the droplets.

*Cannabis* extracts are oily extracts from a plant of the *Cannabis* genus. Preferable cannabis extracts include tetrahydrocannabinol (THC), cannabidiol (CBD), and other cannabinoids including cannabinol (CBN), cannabigerol (CBG), tetrahydrocannabivarin (THCV), cannabidivarin (CBDV), and cannabichromene (CBC). Preferred cannabis extracts include at least 30% by weight THC and/or CBD, while more preferred cannabis extracts include at least 60% by weight THC and/or CBD. Most preferred cannabis extracts include at least 80% by weight THC and/or CBD.

Preferable terpenes include monoterpenes (incorporate two isoprene units and have the molecular formula $C_{10}H_{16}$), monoterpenoids, diterpenes (incorporate four isoprene units and often have the molecular formula $C_{20}H_{32}$), and diterpenoids. Preferable terpenes for inclusion in the microemulsion 336 include limonene, pinene, linalool, beta-caryophyllene, retinol, phytol, myrcene, humulene, ocimene, terpinolene, geraniol, and geranylgeraniol.

The alcohol lipid mixture 312 optionally may include an alcohol-soluble deliverable that is a solid at room temperature and pressure. Thus, unlike the oil-soluble species 311 that is a liquid at room temperature and pressure or heated and solubilized in oil as previously described, the alcohol-soluble deliverable is a solid at room temperature and pressure. Preferably, the alcohol-soluble deliverable is less soluble in the oil than the oil-soluble species 311. Such alcohol-soluble deliverables are solubilized in the modified oil phase droplets of the microemulsion, thus in the alcohol lipid mixture 312 with the oil-soluble species 311.

Alcohol-soluble deliverables include some plant sterols, some polyphenols, and some anti-microbials. Preferable plant sterols include *Tribulus terrestris* and yohimbe. Preferable polyphenols include resveratrol, pterostilbene, curcumin, *Boswellia*, and quercetin. Preferable anti-microbials include artemisinin, monolaurin, and Andrographis. Preferably, these alcohol-soluble deliverables are incorporated into the alcohol lipid mixture 312 of the microemulsion 336 as a solid in powder form.

The modified polar continuous phase 322 may include a water-soluble deliverable specie or species that is more soluble in water than the oil-soluble species 311. Such water-soluble deliverables are solubilized in the modified polar continuous phase 322 of the microemulsion 336. On subsequent dilution of the microemulsion 336 to form the high-water content beverage 342, the water-soluble deliverable specie or species solubilizes in the modified water phase of the beverage.

The phospholipid and the polyethylene glycol derivative in combination form the boundary between the modified polar continuous phase and the interior of the modified oil phase droplets of the high-water content beverage 342. To maintain the desired alcohol concentration within the droplets, thus reducing the likelihood of losing the alcohol to the modified polar continuous phase and the associated dissociation of the oil-soluble species from the droplets, the phospholipid, polyethylene glycol derivative, and the ratio between the two are important, as previously discussed.

The phospholipid of the alcohol-lipid mixture 312 is a glycerophospholipid preferably isolated from lecithin. As the phospholipid is preferably a lecithin isolate, the named isolates preferably include 80% (w/w) of the specified phospholipid with the remaining constituents being one or more additional phospholipids isolated from the lecithin or other lecithin isolates. Preferred phospholipid lecithin isolates include phosphatidylcholine (PC), phosphatidylethanolamine (PE), phosphatidylinositol (PI), ceramide phosphoryl ethanolamine (Cer-PE), ceramide phosphoryl choline (SPH), and combinations thereof, with PC, PE, and combinations thereof being more preferred. However, all phospholipid lecithin isolates are unexpectedly not interchangeable in forming shelf-stable and visually clear MOIW microemulsions, as the phosphatidylserine (PS) and phosphatic acid (PA) isolates are not useful when both shelf-stable and visually clear MOIW microemulsions are desired. When the oil-soluble species 311 is cannabis extracts, the phospholipid is preferably PC.

The phospholipid may be present in the high-water content beverage 342 from 0.001% to 0.3% on a weight basis. Preferably, the phospholipid constitutes from 0.002% to 0.04% of the high-water content beverage 342 on a weight basis. When the oil-soluble species is cannabis extracts and the water content is approximately 99% by weight, the phospholipid constitutes from 0.003% to 0.05% of the high-water content beverage 342 on a weight basis.

The polyethylene glycol derivative of the alcohol-lipid mixture 312 may be a polyethylene glycol modified vitamin E, such as tocopheryl polyethylene glycol succinate 1000 (TPGS), polysorbate 40, polysorbate 60, or polysorbate 80. Preferably, the polyethylene glycol derivate is TPGS, polysorbate 60, or polysorbate 80. More preferably, the polyethylene glycol derivative is TPGS or polysorbate 80. When the oil-soluble species is cannabis extracts, the preferred polyethylene glycol derivative is TPGS.

The polyethylene glycol derivative may be present in the high-water content beverage 342 from 0.001% to 0.6% on a weight basis. Preferably, the polyethylene glycol derivative constitutes from 0.001% to 0.4% of the high-water content beverage 342 on a weight basis. When the oil-soluble species is cannabis extracts, the polyethylene glycol derivative is polysorbate 80, and the water content is approximately 99% by weight, the polyethylene glycol derivative constitutes from 0.001% to 0.1% of the high-water content beverage 342 on a weight basis.

TPGS, polysorbate 20, polysorbate 40, polysorbate 60, and polysorbate 80 are often thought of as interchangeable surfactants. This was determined not to be the case in the formation of the described high-water content beverage 342 when a shelf-stable and visually clear beverage microemulsion is desired.

When used in conjunction with the phospholipid, TPGS resulted in shelf-stable and visually clear beverage microemulsions at phospholipid to TPGS ratios of approximately 1:0.4 to 1:4 by weight, with preferred shelf-stable MOIHW microemulsions being formed at ratios of 1:1.6 to 1:4 by weight. When used in conjunction with the phospholipid, polysorbate 20 did not reproducibly form shelf-stable and visually clear beverage microemulsions. When used in combination with the phospholipid, polysorbate 40 resulted in shelf-stable and visually clear beverage microemulsions at PC to polysorbate 40 ratios of approximately 1:2 to 1:3 by weight, with preferred shelf-stable MOIHW microemulsions being formed at a ratio of approximately 1:3 by weight. When used in combination with the phospholipid, polysorbate 60 resulted in shelf-stable and visually clear beverage microemulsions at phospholipid to polysorbate 60 ratios of approximately 1:2 to 1:4 by weight, with preferred shelf-stable MOIHW microemulsions being formed at a ratio of 1:2 to 1:3 by weight. When used in combination with the phospholipid, polysorbate 80 resulted in shelf-stable and visually clear beverage microemulsions at phospholipid to polysorbate 80 ratios of approximately 1:0.4 to 1:4 by weight, with preferred shelf-stable MOIHW microemulsions being formed at a ratio of 1:0.6 to 1:4 by weight.

These results establish that the multiple polyethylene glycol derivatives are unexpectedly not interchangeable in forming shelf-stable and visually clear MOIHW microemulsions. In fact, polysorbate 20 is not useful to reproducibly form shelf-stable and visually clear MOIHW microemulsions. Furthermore, TPGS and polysorbate 80 are the preferred polyethylene glycol derivatives as in combination with the phospholipid, they provide the desired shelf-stable and visually clear beverage microemulsions over the widest oil-soluble species concentration range.

The alcohol-lipid mixture 312 preferably includes at least one oil held within the phospholipid/polyethylene glycol derivative monolayer. The oil may be an MCT oil, a citrus oil, and combinations thereof. MCT oils are triglycerides whose fatty acids have an aliphatic tail of 6-12 carbon atoms. Preferable MCT oils include caproic acid (hexanoic acid), caprylic acid (octanoic acid), capric acid (decanoic acid), lauric acid (dodecanoic acid), and combinations thereof. More preferred MCT oils include caprylic acid, capric acid, and combinations thereof. Preferred citrus oils include orange oil, lemon oil, and combinations thereof. When the oil-soluble species is cannabis extracts, the oil is preferably a combination of caprylic and capric acids.

The oil may be present in the high-water content beverage 342 from 0.001% to 0.6% on a weight basis. Preferably, the oil constitutes from 0.001% to 0.4% of the high-water content beverage 342 on a weight basis. When the oil-soluble species is cannabis extracts, the polyethylene glycol derivative is polysorbate 80, and the water content is approximately 99% by weight, the oil constitutes from 0.001% to 0.1% of the high-water content beverage 342 on a weight basis.

The high-water content beverage 342 includes at least one alcohol. The preferable alcohol is food grade as the high-water content beverage 342 is ingestible and edible. Preferably, the alcohol is ethanol, with USP food grade 190 proof (95% ethanol, 5% water) ethanol being more preferred. Alcohol water contents in excess of 10% are less preferred for the alcohol, as then the additional water should be considered in relation to the total water content of the high-water content beverage 342.

The alcohol may be present in the high-water content beverage 342 from 0.002% to 1.2% on a weight basis. Preferably, the alcohol constitutes from 0.002% to 0.8% of the high-water content beverage 342 on a weight basis. When the oil-soluble species is cannabis extracts, the polyethylene glycol derivative is polysorbate 80, and the water content is approximately 99% by weight, the alcohol constitutes from 0.002% to 1.2% of the high-water content beverage 342 on a weight basis.

The modified oil phase droplets of the intermediate low-water content microemulsion 336 may be considered to have a high alcohol content, thus having an oil to alcohol weight ratio of from 1:1.5 to 1:4, preferably from 1:1.5 to 1:3 by weight.

The modified polar continuous phase 322 includes a sugar or sugar alcohol and water. By "sugar or sugar alcohol" it is meant a sugar or a sugar alcohol preferably including from 3 to 12 carbon atoms that is a liquid at room temperature or soluble in water at room temperature. Preferable sugars include sucrose, cane sugar, and pure maple syrup, with pure maple syrup being preferred due to the inclusion of tree resins. Preferable sugar alcohols have from 3 to 6 carbon atoms and include glycerol (glycerin).

While one could expect additional sugar alcohols, including xylitol, erythritol, mannitol, and sorbitol to be useful in forming the high-water content beverage 342, all sugar alcohols are unexpectedly not interchangeable in forming shelf-stable and visually clear MOIHW microemulsions, as xylitol, erythritol, mannitol, and sorbitol are not useful when both shelf-stable and visually clear microemulsions are desired. Thus, preferred sugar or sugar alcohols include sucrose, cane sugar, pure maple syrup, glycerol, and combinations thereof. More preferred sugar or sugar alcohols include pure maple syrup, glycerol, and combinations thereof. Presently, the most preferred sugar or sugar alcohol is glycerol.

When the sugar or sugar alcohol is glycerol, the ratio of glycerol to water is from 1:35,000 to 1:45 by weight, preferably from 1:30,000 to 1:45 by weight. When the sugar or sugar alcohol is pure maple syrup, sucrose, or cane sugar, and water is present in the syrup or used to solubilize the sucrose or cane sugar, this additional water becomes part of the water constituent of the high-water content beverage 342 and is thus included in the sugar or sugar alcohol to water weight ratio as water.

When the sugar or sugar alcohol is glycerol and the total water content of the high-water content beverage 342 is at least 95% by weight, the glycerol may be present in the high-water content beverage 342 from 0.003% to 2.4%, preferably from 0.003% to 2.3% on a weight basis. When the total water content of the high-water content beverage 342 is at least 97% by weight, the glycerol may be present in the microemulsion 336 from 0.003% to 1.6%, preferably from 0.002% to 1.5% on a weight basis. When the total water content of the high-water content beverage 342 is at least 99% by weight, the glycerol is preferably present in the microemulsion 336 from 0.003% to 0.4% on a weight basis.

The high-water content beverage 342 may optionally include additional ingredients to modify the taste or color of the beverage and/or preservatives that are chemically compatible with the oil-soluble species and do not substantially interfere with the separation between the modified oil and water phases of the microemulsion. Such additional ingredients may include flavorants, colorants, thickeners, preservatives, antioxidants, electrolytes, and perfumes. Other compatible additional ingredients may be used in the microemulsion.

The following examples are provided to illustrate one or more preferred embodiments of the invention. Numerous variations can be made to the following examples that lie within the scope of the invention.

EXAMPLES

Example 1: Constituents of a MOIHW Microemulsion Including *Cannabis* Extracts as the Oil-Soluble Species MOIHW microemulsions were prepared as beverages having an approximate 470 mL (16 oz.) total volume. Three different beverage forms were prepared as MOIHW microemulsions, a first including carbon dioxide to provide a sparkling water, a second including tea to provide a tea, and a third including non-alcoholic beer to provide a cannabinoid infused beer.

Regardless of beverage form, the MOIHW microemulsion beverage included either cannabis extracts including approximately 3 mg of THC, cannabis extracts including approximately 7 mg of CBD, or cannabis extracts including approximately 3 mg of THC and 7 mg of CBD to provide a total cannabinoid beverage content of 10 mg. Each beverage also included from 3 mg to 20 mg of PC, from 17 mg to 70 mg of ethanol, from 35 mg to 150 mg of glycerin, from 7 mg to 38 mg of medium chain triglycerides, and approximately 470 mL of water to provide an approximately 99.8% water by weight beverage. TPGS was included to provide the desired physical structures in the MOIHW microemulsion, but polysorbate 80 also is preferred.

Example 2: A Method of Making MOIHW Microemulsion Including *Cannabis* Extracts Approximately 3 mg, 7 mg, or 10 mg of cannabinoid, as referenced in Example 1, was combined in MCT oil and then combined with TPGS, PC, glycerin, and ethanol in enough water to form a low-water content microemulsion. The low-water content microemulsion was then mixed with additional water to form the MOIHW microemulsion in beverage form.

Example 3: Comparative Blood Uptake Rates for Oral Delivery of the *Cannabis* Extract THC, CBD, and a Combination of THC and CBD from the Consumed Beverage A THC beverage, a CBD beverage, and a mixed CBD/THC beverage were compared from a THC, CBD, or CBD/THC blood uptake rate perspective.

On an empty stomach, human subjects consumed approximately 470 mL of the THC, CBD, or CBD/THC beverage over a 20-minute period. Blood samples were collected from the subjects before the 20-minute period of beverage consumption initiated and at varying time intervals between approximately 20- and 200-minutes after completion of the 20-minute beverage consumption period. The collected blood samples were analyzed for the concentration of THC, CBD, or CBD/THC using LCMS.

Figure 4A:
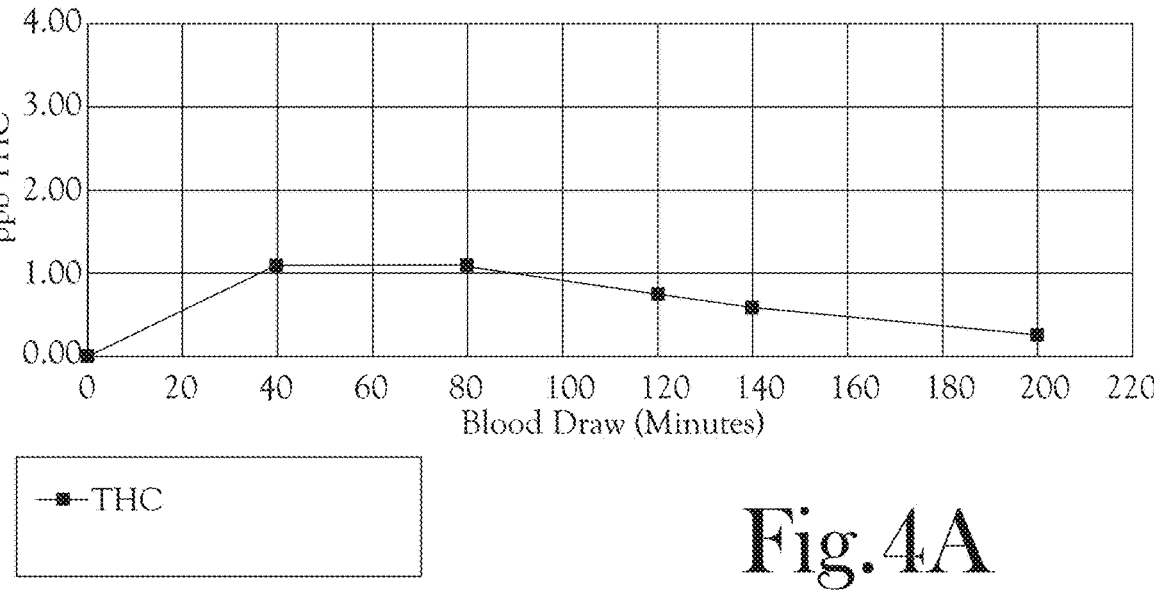
FIG. 4A provides the results from the THC MOIHW microemulsion beverage for THC blood uptake rate and concentration analysis in graphical form.
Figure 4B:
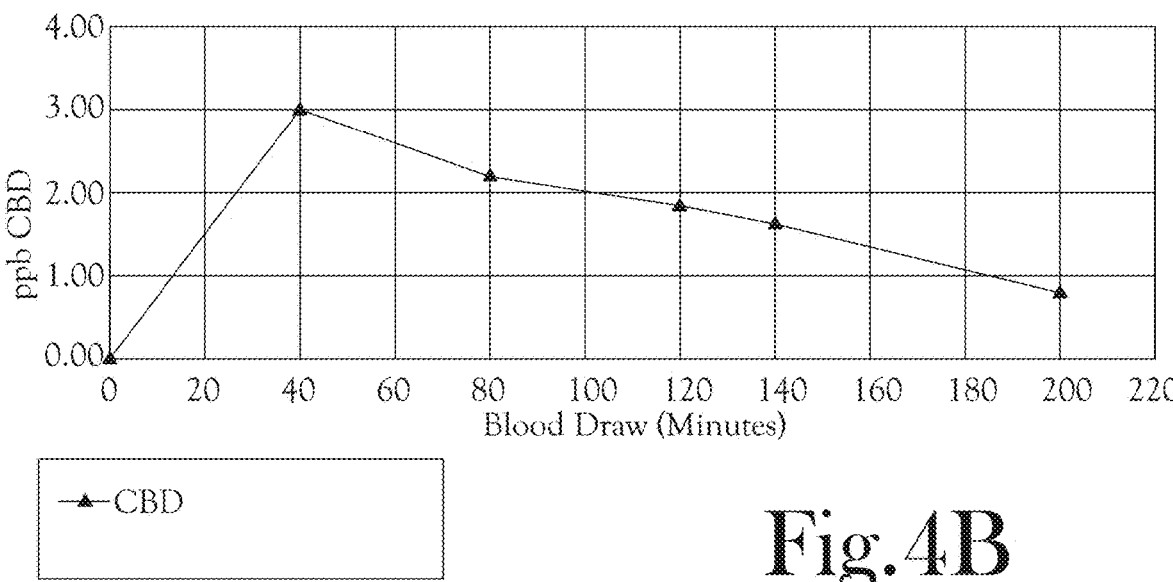
FIG. 4B provides the results from the CBD MOIHW microemulsion beverage for CBD blood uptake rate and concentration analysis in graphical form.
Figure 4C:
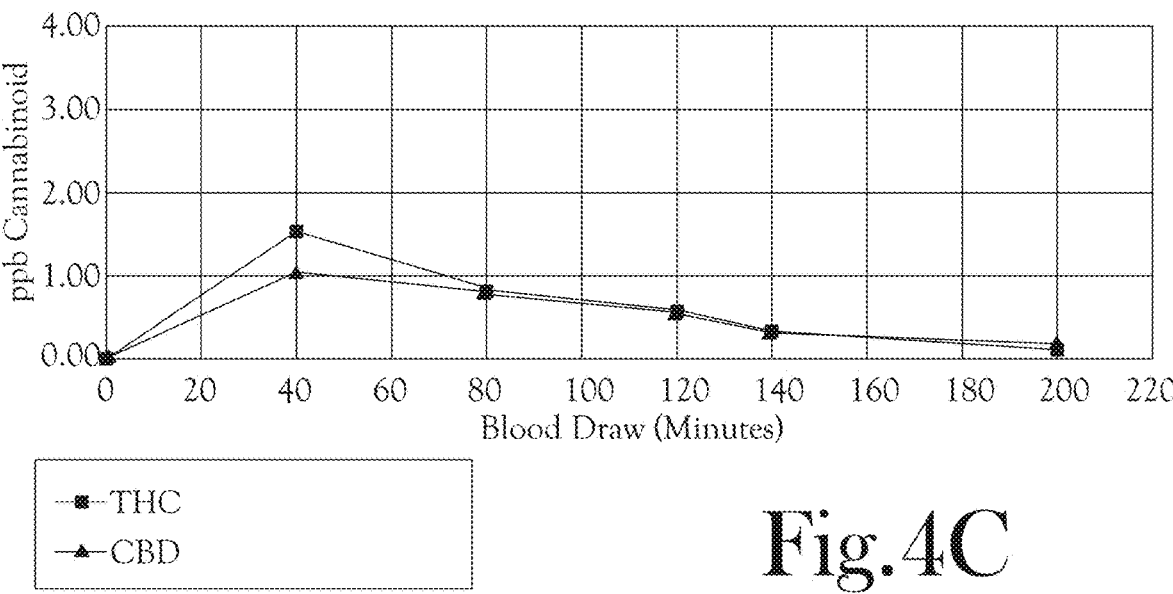
FIG. 4C provides the results from the CBD/THC MOIHW microemulsion beverage for CBD and THC blood uptake rate and concentration analysis in graphical form.

FIG. 4A provides the results from the THC MOIHW microemulsion beverage for THC blood uptake rate and concentration analysis in graphical form. The time after the subject began consuming the beverage when the blood sample was collected is represented on the X-axis, while the average parts-per-billion (ppb) of cannabinoid determined for the blood samples is represented on the Y-axis. FIG. 4B provides the results from the CBD MOIHW microemulsion beverage for CBD blood uptake rate and concentration analysis in graphical form. FIG. 4C provides the results from the CBD/THC MOIHW microemulsion beverage for CBD and THC blood uptake rate and concentration analysis in graphical form.

FIG. 4A established that maximum THC blood concentration was achieved after approximately 40-minutes and lasted until approximately 80-minutes. From the approximately 3 mg of THC consumed, the MOIHW microemulsion beverage provided a THC blood concentration in excess of one parts-per-billion (ppb) within 40 minutes of consumption. FIG. 4B established that maximum CBD blood concentration was achieved after approximately 40-minutes and remained close to the maximum until approximately 80-minutes. From the approximately 7 mg of CBD consumed, the MOIHW microemulsion beverage provided a CBD blood concentration in excess of 2 ppb (approximately 3 ppb) within 40 minutes of consumption. Interestingly, FIG. 4C established that the combination of CBD with THC resulted in the maximum blood concentration for both being achieved at approximately 40-minutes.

The beverage consuming subjects also were asked at what time did they feel an effect from the beverage, and at what time did that feeling reach a peak. Averaged results from this survey of the subjects is presented below in Table I.

TABLE I

|  | THC Beverage | CBD Beverage | CBD/THC Beverage |
|---|---|---|---|
| Average Onset Feeling | 25 minutes | 10 minutes | 20 minutes |
| Average Peak Feeling | 48 minutes | 30 minutes | 30 minutes |

Thus, in addition to the MOIHW microemulsion demonstrating the ability to deliver the cannabinoid extract to the bloodstream at an approximately maximum level within 40-minutes after beginning consumption of the beverage, it was established that consumers of the beverage begin to feel the effect of the beverage within approximately 20-minutes and attain a peak feeling within an hour.

Figure 5:
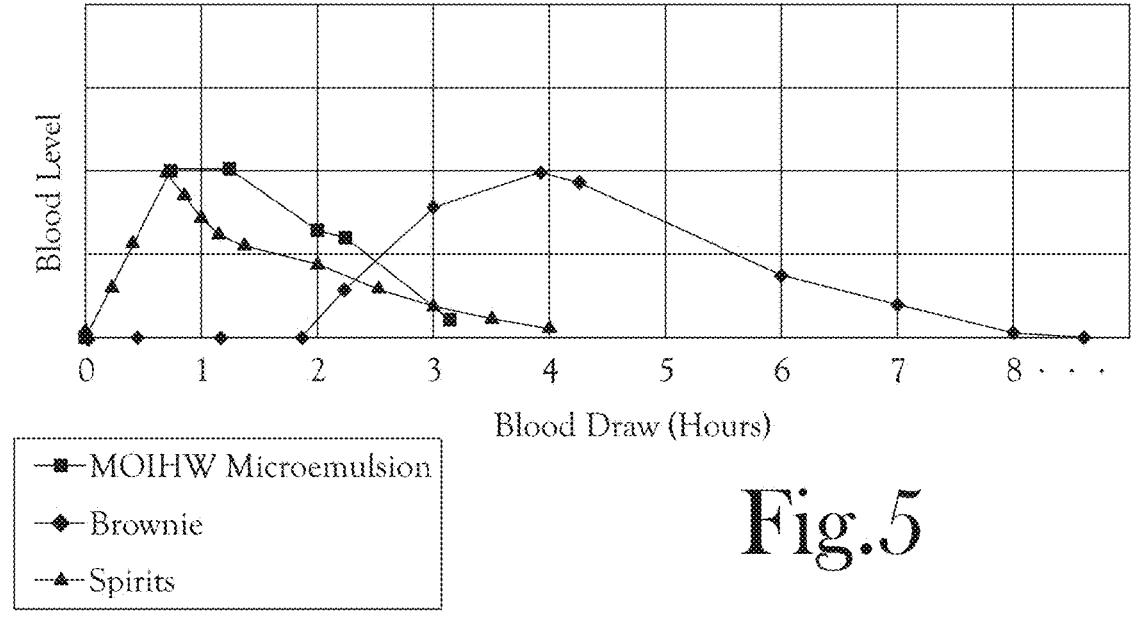
FIG. 5 provides alcohol blood concentrations and time data after consumption and THC blood concentrations and time data after consumption of an oil-based delivery system superimposed with the THC MOIHW microemulsion beverage data from FIG. 4A.

Example 4: Comparative Blood Uptake Rates for Oral Delivery of the *Cannabis* Extract THC in a MOIHW Microemulsion Beverage Versus Alcohol in Liquor, Wine, and Beer Forms FIG. 5 provides alcohol blood concentrations and time after consumption data taken from Mitchell et al., *Absorption and Peak Blood Alcohol Concentration After Drinking Beer, Wine, or Spirits*, Alcohol Clin Exp Res, Vol. 38, No. 5 (2014); pp. 1200-1204 and THC blood concentrations and time after consumption of an oil-based delivery system (brownie) taken from Vandrey et al., Pharmacokinetic Profile of Oral *Cannabis* in Humans: Blood and Oral Fluid Disposition and Relation to Pharmacodynamic Outcomes, Journal of Analytical Toxicology, Vol. 41 (2017); pp. 83-99 superimposed with the THC MOIHW microemulsion beverage data from FIG. 4A. While the Y-axis actual concentration values lose relevance in this comparison, and were thus approximately leveled in the figure, the time peak blood concentrations are reached after consumption and the associated decay remain meaningful for comparison.

As can be seen from this comparison, the alcohol-based beverage (spirits in water) reached a maximum concentration within approximately 30 minutes to an hour and the oil-based THC delivery brownie reached a maximum concentration just before 3 hours, while the THC based beverage reached a maximum concentration within approximately 40 minutes. For the alcohol-based beverage, the maximum concentration was reduced by approximately half, thus half-life, after 2 hours of consumption, while for the brownie the half-life was reached approximately 6 hours after consumption. For the THC based beverages, the maximum concentration was reduced by approximately half after close to 3 hours.

The maximum blood concentrations for the alcohol-based beverages (30 min.) and the THC MOIHW microemulsion beverages (40-min.) are comparable and could be readily managed by the user. In comparison, the oil-based THC brownie failed to deliver a maximum blood concentration until approaching 3 hours. While the decrease is blood concentration is not as rapid for the THC beverage as for the alcohol beverage, it is substantially quicker than for the oil-based brownie, which has a half-life approximating 6 hours after consumption.

From a feeling perspective, the THC MOIHW micro-emulsion beverages provided onset within about 25 minutes and a peak within about 48 minutes, while the oil-based THC brownie provided an onset after about an hour that did not peak until approximately 3 hours. Thus, the MOIHW microemulsion based beverages provide a consumer with the ability to manage the consumption/effect relationship similarly to that of alcohol-based beverages, unlike with the consumption of oil-based deliverables.

To provide a clear and more consistent understanding of the specification and claims of this application, the following definitions are provided.

High-water content means including at least 95% water by weight, preferably at least 97% water by weight, and more preferably at least 99% water by weight.

Intra-oral delivery means that a substantial portion of the delivery into the bloodstream that occurs upon oral administration of the liquid including the deliverable occurs by transmucosal absorption through the mouth, throat, and esophagus before the liquid reaches the stomach. For droplets to be considered suitable for intra-oral delivery, the average droplet diameter is at most 125 nm. Intra-oral delivery is believed to increase with decreasing average droplet diameter, with average droplet diameters of approximately 25 nm being preferred.

An oil-soluble species is a species that is insoluble in water and soluble in medium chain triglyceride (MCT) oils at 50 mg/mL and higher, preferably 100 mg/mL and higher. Oil-soluble species are generally soluble in MCT oils at room temperature and are freely or very soluble in MCT oils at temperatures of 70 degrees Celsius and greater. The term "generally soluble in MCT oils at room temperature" is used because some high purity oil-soluble species are sparingly soluble in MCT oils at room temperature, but are freely or very soluble in the MCT oils above 70 degrees Celsius, and once solubilized in the MCT oils at elevated temperature, will remain solubilized at room temperature. Oil-soluble species are preferably pharmacologically active, more preferably are a drug or a supplement, and neither include nor are water. Thus, liquids and solids may exist that technically are soluble in oil, but because they also are soluble in water or not sufficiently soluble in MCT oils are not "oil-soluble species".

Phosphatidylcholine (PC) molecules are a subset of the larger set of phospholipids and are commonly used to form liposomes in water. When placed in water without other constituents, PC forms liposomes. In the presence of an oil, the application of sufficient shear forces to the PC liposomes in water can produce monolayer structures, including micelles. PC has a head that is water-soluble and a tail that is much less water-soluble in relation to the head. PC is a neutral lipid, but carries an electric dipole moment of about 10 D between the head and the tail, making the molecule itself polar.

Tocopheryl polyethylene glycol succinate 1000 (TPGS) is generally considered a surfactant having a non-polar, oil-soluble "Vitamin E" tail and a polar, water-soluble polyethylene glycol head. TPGS is a member of the polyethylene glycol derivatives that also include polysorbate 20, 40, 60, and 80.

Room temperature and pressure means from 20 to 28 degrees Celsius at approximately 100 kPa.

Solid means a substance that is not a liquid or a gas at room temperature and pressure. A solid substance may have one of a variety of forms, including a monolithic solid, a powder, a gel, or a paste.

Liquid means a substance that is not a solid or a gas at room temperature and pressure. A liquid is an incompressible substance that flows to take on the shape of its container.

Solutions lack an identifiable interface between the solubilized molecules and the solvent. In solutions, the solubilized molecules are in direct contact with the solvent.

Solubilized means that the oil-soluble species to be delivered is in the solution of the droplet. When solubilized, dissociation (thus, liquid separation or solid formation) of the oil-soluble species does not result in droplet average particle diameters in excess of 200 nm as determined by DLS and discussed further below, or by the formation of precipitated crystals of the oil-soluble species visible with the naked eye. Thus, if either average particle diameters in excess of 200 nm or precipitated crystals visible to the naked eye form, the oil-soluble species is not solubilized in the solution of the droplet. If an oil-soluble species is not solubilized in the solution, it is insoluble in the solution. In many respects, solubility may be thought of as a concentration dependent continuum. For example, the following descriptive terms may be used to express solubility of a solute in a solvent (grams solid/mL of solvent) at 25 degrees Celsius:

TABLE 1

| Descriptive Level | Parts solvent per 1 part of solute |
| --- | --- |
| Very Soluble | Less than 1 |
| Freely Soluble | From 1 to 10 |
| Soluble | From 10 to 30 |
| Sparingly Soluble | From 30 to 100 |
| Slightly Soluble | From 100 to 1000 |
| Very Slightly Soluble | From 1000 to 10,000 |
| Insoluble | More than 10,000 |

Dissociation occurs when a previously solubilized solid or liquid leaves a solution and is no longer in direct contact with a solvent of the solution. Dissociation of solids from the solvent occurs through recrystallization, precipitation, and the like. Dissociation of liquids from the solvent occurs through separation and the formation of a visible meniscus between the solvent and the dissociated liquid.

A shelf-stable microemulsion may be determined in one of two ways. One way to establish that a microemulsion stored in a sealed container substantially excluding air and moisture is shelf-stable is when dissociation of a solid does not occur and the oil phase droplets in the water do not change in average diameter by more than +/−20% at about 25° C. for a time period of at least 3 months to 2 years, preferably for a time period of at least 6 months to 2 years, and more preferably, for a time period of at least 1 year to 2 years. Another way to establish that a microemulsion is shelf-stable is when dissociation of a solid does not occur and the oil phase droplets in the water do not separate into a visibly distinct phase with a visible meniscus when stored in a sealed container substantially excluding air and moisture at about 25° C. for a time period of at least 6 months to 2 years, and more preferably, for a time period of at least 1 year to 2 years. Either type of dissociation means that the microemulsion is not shelf-stable.

A visually clear microemulsion has an average particle diameter of 200 nm and less and lacks precipitated solid crystals visible to the naked eye.

Emulsions are mixtures of two or more liquids that do not solubilize. Thus, one of the liquids carries droplets of the second liquid. The droplets of the second liquid may be said to be dispersed in a continuous phase of the first liquid. An interface, separation, or boundary layer exists between the carrier liquid (continuous phase) and the droplets of the second liquid. Emulsions may be macroemulsions, pseudo-emulsions, microemulsions, or nanoemulsions. The primary differences between macroemulsions, microemulsions, and nanoemulsions are the average diameter of the droplets dispersed in the continuous phase and the stability of the emulsion over time. Pseudo-emulsions are differentiated as solids are present in the emulsion.

Droplets or liquid particles are formed by the hydrophobic "oil" phase of a microemulsion and are carried by the hydrophilic continuous phase. The exterior of the droplets is defined by a boundary layer that surrounds the volume of each liquid droplet. The boundary layer of a droplet defines the exterior surface of the droplets forming the dispersed oil phase of the microemulsion. The continuous phase of the microemulsion resides exterior to the boundary layer of the droplets, and thus, carries the droplets.

Macroemulsions are thermodynamically unstable but kinetically stable dispersions of oil in water, with oil being defined as any water-insoluble liquid. By thermodynamically unstable it is meant that once created, the macroemulsion is always reverting to the original, immiscible state of the oil and water constituents (demulsification), but this break down is slow enough (thus, kinetically "stable") that the macroemulsion may be considered stable from an intended use practicality perspective. Macroemulsions scatter light effectively and therefore appear milky, because their droplets are greater in diameter than the wavelength of visible light. The droplets of a macroemulsion usually have average droplet diameters from 10 to 50 micrometers. The IUPAC definition of a macroemulsion is an "emulsion in which the particles of the dispersed phase have diameters from approximately 1 to 100 micrometers. Macro-emulsions comprise large droplets and thus are "unstable" in the sense that the droplets sediment or float, depending on the densities of the dispersed phase and dispersion medium."

Pseudo-emulsions are dispersions of oil in water, with oil being defined as any water-insoluble liquid, including tiny (micronized) solid granules that are not fully solubilized in the oil droplets. The term "pseudo-emulsion" is used as these mixtures are not true emulsions as the solid granules are not fully solubilized into the droplets. The droplets of a pseudo-emulsion have an average droplet diameter of 1 to 20 micrometers, thus being a "solid granule modified macroemulsion".

Microemulsions are thermodynamically stable dispersions of oil in water, with oil being defined as any water-insoluble liquid. Microemulsion are made by simple mixing of the components. Thus, microemulsions spontaneously form and do not require high shear forces. Unlike macroemulsions, microemulsions do not substantially scatter light. The IUPAC definition of a microemulsion is a "dispersion made of water, oil, and surfactant(s) that is an isotropic and thermodynamically stable system with dispersed domain diameter varying approximately from 1 to 100 nm, usually 10 to 50 nm." Thus, the droplets of a microemulsion are approximately three orders of magnitude smaller than the droplets of a macroemulsion and are thermodynamically stable.

Nanoemulsions have average droplet diameters from 10 to 125 nanometers, thus being at least an order of magnitude smaller in average droplet diameters than macro- and pseudo-emulsions. Transparent nanoemulsions have average droplet diameters from 10 to 100 nanometers. Nanoemulsions are made with mechanical, high shear forces. While the average droplet diameter of nanoemulsions and microemulsions formally overlap, in practice, the average droplet diameter of nanoemulsions are or become larger than those of microemulsions, as lacking the thermodynamic stability of microemulsions, the average droplet diameter of nanoemulsions is forever increasing.

Continuous phase means the portion of a microemulsion that carries the droplets that include the substance to be delivered. For example, the modified oil-in-water microemulsions (non-polar droplets in polar continuous phase) addressed herein have oil droplets including the oil-soluble species to be delivered carried in a polar, "water" continuous phase. While the words "water" and "oil" are used, the "water" can be any liquid that is more polar than the "oil" (such as a polar oil), and the "oil" can be any liquid that is less polar than the "water. Thus, the terms "polar continuous phase" and "water continuous phase" are synonymous, unless water is specifically being discussed as one of the microemulsion components.

Average droplet diameter is determined by dynamic light scattering, sometimes referred to a photon correlation spectroscopy. The determination is made between 20 and 25 degrees Celsius. One example of an instrument suitable for average droplet diameter determination is a Nicomp 380 ZLS particle sizer as available from Particle Sizing Systems, Port Richey, FL DLS can determine the diameter of droplets in a liquid by measuring the intensity of light scattered from the droplets to a detector over time. As the droplets move due to Brownian motion the light scattered from two or more droplets constructively or destructively interferes at the detector. By calculating the autocorrelation function of the light intensity and assuming a droplet distribution, it is possible to determine the sizes of droplets from 1 nm to 5 um. The instrument is also capable of measuring the Zeta potential of droplets.

Ingestible means capable of being ingested through the mouth by a living mammal while edible means fit to be eaten, thus in contrast to being unpalatable or poisonous. Edible also means that the composition has less than the permitted amount of viable aerobic microorganisms and meets the American Herbal Products Association (AHPA) guidelines for metals, adulterants, toxins, residual solvents, and pesticides.

Where a range of values is provided, it is understood that each intervening value, to the tenth of the unit of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

While various aspects of the invention are described, it will be apparent to those of ordinary skill in the art that other aspects and implementations are possible within the scope of the invention.

What is claimed is:

1. A high-water content beverage composition for oral consumption by a human subject, the composition comprising:

an oil-soluble species; and a modified oil-in-water microemulsion including a modified oil phase and a modified polar continuous phase, where the oil-soluble species is solubilized in the modified oil phase, the modified oil phase comprising a phospholipid, a polyethylene glycol derivative, an oil, and ethanol, where the modified polar continuous phase comprises a sugar or sugar alcohol and water, and where the high-water content beverage comprises at least 95% water by weight, where the polyethylene glycol derivative is chosen from a polyethylene glycol modified vitamin E, tocopheryl polyethylene glycol succinate 1000 (TPGS), polysorbate 60, polysorbate 80, and combinations thereof, where a ratio of the phospholipid to the polyethylene glycol derivative is 1:1.6 to 1:4 by weight, where a ratio of the oil to the ethanol is from 1:1.5 to 1:3 by weight, where the sugar or sugar alcohol is chosen from sucrose, cane sugar, pure maple syrup, glycerol, and combinations thereof, and where the composition is ingestible and edible.

2. The composition of claim 1, where the modified oil-in-water microemulsion is visually clear.

3. The composition of claim 1, where the modified oil-in-water microemulsion is shelf-stable.

4. The composition of claim 1, the modified oil-in-water microemulsion configured to provide uptake of the oil-soluble species to the bloodstream of a human at an effective bloodstream concentration through the oral and gastric mucosa of the human subject.

5. The composition of claim 1, where the modified oil phase is configured so the modified oil phase better solubilizes the oil-soluble species than the oil alone.

6. The composition of claim 1, where the modified oil phase is dispersed in the modified polar continuous phase.

7. The composition of claim 6, where droplets of the modified oil phase have an average droplet diameter of 1 to 80 nanometers.

8. The composition of claim 6, where droplets of the modified oil phase have an average droplet diameter of 10 to 40 nanometers.

9. The composition of claim 6, where droplets of the modified oil phase have an approximately bimodal distribution of average droplet diameters.

10. The composition of claim 9, where the bimodal distribution of average droplet diameters includes the average droplet diameter of 1 to 80 nanometers and an average droplet diameter from 90 to 200 nanometers.

11. The composition of claim 1, where the oil-soluble species is chosen from a *cannabis* extract, terpenes, vitamins, and combinations thereof.

12. The composition of claim 11, the *cannabis* extract chosen from, cannabidiol, tetrahydrocannabinol, other cannabinoids, and combinations thereof.

13. The composition of claim 11, where the *cannabis* extract comprises cannabidiol and tetrahydrocannabinol.

14. The composition of claim 11, the terpenes chosen from limonene, pinene, linalool, beta-caryophyllene, retinol, phytol, myrcene, humulene, ocimene, terpinolene, geraniol, and geranylgeraniol, and combinations thereof.

15. The composition of claim 1, where the phospholipid is a glycerophospholipid isolated from lecithin.

16. The composition of claim 15, where the phospholipid is chosen from phosphatidylcholine, phosphatidylethanolamine, phosphatidylinositol, ceramide phosphoryl ethanolamine, ceramide phosphoryl choline (SPH), and combinations thereof.

17. The composition of claim 15, where the phospholipid is chosen from phosphatidylcholine, phosphatidylethanolamine, and combinations thereof.

18. The composition of claim 15, where the phospholipid is at least 80% by weight phosphatidylcholine.

19. The composition of claim 1, where the polyethylene glycol derivative is tocopheryl polyethylene glycol succinate 1000.

20. The composition of claim 1, where the polyethylene glycol derivative is chosen from tocopheryl polyethylene glycol succinate 1000, polysorbate 80, and combinations thereof.

21. The composition of claim 1, where the polyethylene glycol derivative is polysorbate 80.

22. The composition of claim 1, the oil chosen from a medium chain triglyceride, a citrus oil, and combinations thereof.

23. The composition of claim 22, the medium chain triglyceride chosen from caproic acid (hexanoic acid), caprylic acid (octanoic acid), capric acid (decanoic acid), lauric acid (dodecanoic acid), and combinations thereof.

24. The composition of claim 22, the medium chain triglyceride chosen from caprylic acid, capric acid, and combinations thereof.

25. The composition of claim 22, the citrus oil chosen from orange oil, lemon oil, and combinations thereof.

26. The composition of claim 1, where the alcohol is 95% ethanol by weight.

27. The composition of claim 1, the sugar or sugar alcohol chosen from pure maple syrup, glycerol, and combinations thereof.

28. The composition of claim 1, where the sugar or sugar alcohol is glycerol.

29. The composition of claim 1, where the oil-soluble species comprises from 0.0001% to 0.24% of the composition by weight.

30. The composition of claim 1, where the oil-soluble species comprises from 0.0001% to 0.04% of the composition by weight.

31. The composition of claim 1, where a ratio of the phospholipid, to the oil, to the polyethylene glycol derivative, to the alcohol, and to the sugar or sugar alcohol is 0.001-0.3:0.001-0.6:0.001-0.6:0.002-1.2:0.003-2.4±10% by weight, when the water is ≥95% by weight.

32. The composition of claim 1, where a ratio of the phospholipid, to the oil, to the polyethylene glycol deriva- tive, to the alcohol, and to the sugar or sugar alcohol is 0.003-0.05:0.001-0.1:0.001-0.1:0.002-0.2:0.003-0.4±10% by weight, when the water is ≥99% by weight.

33. The composition of claim 1, where the phospholipid comprises from 0.0005% to 0.45% of the composition by weight.

34. The composition of claim 1, where the phospholipid comprises from 0.005% to 0.075% of the composition by weight.

35. The composition of claim 1, where the polyethylene glycol derivative comprises from 0.001% to 0.6% of the composition by weight.

36. The composition of claim 1, where the polyethylene glycol derivative comprises from 0.001% to 0.1% of the composition by weight.

37. The composition of claim 1, where the oil comprises from 0.001% to 0.6% of the composition by weight.

38. The composition of claim 1, where the oil comprises from 0.001% to 0.1% of the composition by weight.

39. The composition of claim 1, where the alcohol com- prises from 0.002% to 1.2% of the composition by weight.

40. The composition of claim 1, where the sugar or sugar alcohol comprises from 0.003% to 2.4% of the composition by weight.

41. The composition of claim 1, where the sugar or sugar alcohol comprises from 0.003% to 0.4% of the composition by weight.

42. The composition of claim 1, where the sugar or sugar alcohol is glycerol and a ratio of the glycerol to the water is from 1:35,000 to 1:45 by weight.

43. The composition of claim 1, where the water com- prises at least 97% of the composition by weight.

44. The composition of claim 1, where the water com- prises at least 99% of the composition by weight.

45. The composition of claim 1, the composition config- ured to provide a human subject a tetrahydrocannabinol blood concentration exceeding one ppb within 40-minutes of consuming the composition comprising 3 mg of the oil- soluble species, where the oil-soluble species is tetrahydro- cannabinol.

46. The composition of claim 1, the composition config- ured to provide a human subject a cannabidiol blood con- centration exceeding two ppb within 40-minutes of consum- ing the composition comprising 7 mg of the oil-soluble species, where the oil-soluble species is cannabidiol.

47. The composition of claim 1, the composition config- ured to provide a human subject the ability to feel the effect of the oil-soluble species within 20 minutes of orally con- suming the composition including the oil-soluble species.

48. The composition of claim 1, the composition config- ured to provide a human subject with a bloodstream con- centration half-life of the oil-soluble species within 3 hours of consuming the composition including the oil-soluble species.

49. A method of forming a high-water content beverage composition for oral consumption by a human subject, the method comprising:

combining a phospholipid, a polyethylene glycol deriva- tive, an oil, and ethanol to form an alcohol-lipid mix- ture;

combining a sugar or sugar alcohol and a first aliquot of water to form a modified polar continuous phase;

combining an oil-soluble species with the alcohol-lipid mixture and the modified polar continuous phase at atmospheric pressure to form an intermediate low- water content modified oil-in-water microemulsion;

combining the intermediate low-water content modified oil-in-water microemulsion with a second aliquot of water; and providing the high-water content beverage, where the polyethylene glycol derivative is chosen from a polyethylene glycol modified vitamin E, tocopheryl polyethylene glycol succinate 1000 (TPGS), polysor- bate 60, polysorbate 80, and combinations thereof, where the sugar or sugar alcohol is chosen from sucrose, cane sugar, pure maple syrup, glycerol, and combina- tions thereof, where a ratio of the phospholipid to the polyethylene glycol derivative is 1:1.6 to 1:4 by weight in the alcohol-lipid mixture, and where a ratio of the oil to the ethanol is from 1:1.5 to 1:3 by weight in the alcohol-lipid mixture.

50. A method of delivering an oil-soluble species to the bloodstream of a human subject, the method comprising:

introducing orally to a human subject a high-water con- tent beverage, the high-water content beverage com- prising:

an oil-soluble species, and a modified oil-in-water microemulsion including a modified oil phase and a modified polar continuous phase, where the oil-soluble species is solubilized in the modified oil phase, the modified oil phase compris- ing a phospholipid, a polyethylene glycol derivative, an oil, and ethanol, where the polyethylene glycol derivative is chosen from a polyethylene glycol modified vitamin E, tocopheryl polyethylene glycol succinate 1000 (TPGS), polysorbate 60, polysorbate 80, and com- binations thereof, where a ratio of the phospholipid to the polyethylene glycol derivative is 1:1.6 to 1:4 by weight, and where a ratio of the oil to the ethanol is from 1:1.5 to 1:3 by weight, where the modified polar continuous phase comprises a sugar or sugar alcohol and water, where the sugar or sugar alcohol is chosen from sucrose, cane sugar, pure maple syrup, glycerol, and combinations thereof, and where the high-water content beverage comprises at least 95% water by weight; and delivering the oil-soluble species to the bloodstream of the human subject, where within 40-minutes of the introducing the high- water content beverage, the human subject has an oil-soluble species blood concentration in excess of one ppb when the high-water content beverage composition includes 3 mg of the oil-soluble species.

51. A high-water content, visually clear, and shelf-stable beverage composition for oral consumption by a human subject, the composition comprising:

a cannabinoid extract;

a phospholipid;

a polyethylene glycol derivative, where the polyethylene glycol derivative is chosen from a polyethylene glycol modified vitamin E, tocopheryl polyethylene glycol succinate 1000 (TPGS), polysorbate 60, polysorbate 80, and combinations thereof, where a ratio of the phospholipid to the polyethylene glycol derivative is 1:1.6 to 1:4 by weight:

an oil;

ethanol, where a ratio of the oil to the ethanol is from 1:1.5 to 1:3 by weight;

a sugar or sugar alcohol, where the sugar or sugar alcohol is chosen from sucrose, cane sugar, pure maple syrup, glycerol, and combinations thereof; and at least 95% water by weight, where the beverage composition is ingestible and edible.

52. The method of claim 49, where the combining at atmospheric pressure is performed at room temperature.

53. The method of claim 49, where the combining at atmospheric pressure is performed without shear forces.

54. The method of claim 49, where the oil-soluble species is combined with the alcohol-lipid mixture before the alcohol-lipid mixture is combined with the modified polar continuous phase.

55. The method of claim 49, where the oil-soluble species is combined with the alcohol-lipid mixture after the alcohol-lipid mixture is combined with the modified polar continuous phase.

56. The method of claim 55, where droplets including the oil-soluble species self-assemble in the modified polar continuous phase.

57. The method of claim 49, where the high-water content beverage further comprises an additional ingredient.

58. The method of claim 50, where at least 50% of the delivering is by transmucosal absorption through the mouth, throat, and esophagus before the high-water content beverage reaches the stomach.

59. The method of claim 50, where the oil-soluble species is tetrahydrocannabinol.

60. The method of claim 50, where the oil-soluble species is cannabidiol.

61. The method of claim 50, where the oil-soluble species is a cannabinoid.

\* \* \* \* \*